United States Patent [19]

Pettersen

[11] Patent Number: 4,908,020
[45] Date of Patent: Mar. 13, 1990

[54] SELF-DESTRUCTIVE NON-REUSABLE INJECTION SYRINGE

[75] Inventor: Tor-Erling Pettersen, Bjornemyr, Norway

[73] Assignee: I.D. International A/S, Oslo, Norway

[21] Appl. No.: 239,560

[22] Filed: Sep. 1, 1988

[30] Foreign Application Priority Data

Sep. 15, 1987 [NO] Norway ................................ 873863
Dec. 15, 1987 [NO] Norway ................................ 875234

[51] Int. Cl.⁴ ............................................. A61M 5/00
[52] U.S. Cl. .................................... 604/110; 604/228
[58] Field of Search ................ 604/110, 187, 228, 218

[56] References Cited

U.S. PATENT DOCUMENTS 4,699,614 10/1987 Glazier ................................ 604/110
4,775,363 10/1988 Sandsdalen ......................... 604/228

Primary Examiner—John D. Yasko
Attorney, Agent, or Firm—Kilpatrick & Cody

[57] ABSTRACT

Self-destructive non-reusable injection syringes consisting of a cylinder 1 which has a needle 2 at one end. In the cylinder a plunger head 3 with a plunger shaft 4 is placed, and in connection with the plunger head 3 or the plunger shaft 4, a release mechanism 6 is made which is released after the first use of the syringe. The release mechanism 6 consists of pieces 10, 11, 12 with at least one steering knob 13 which runs along the syringe's axial sloping path or course 14 in another body 15. The path or course 14 is at one end joined to an axially running path 16 which is open at the end 17 of the body 15. A stopper 17 for the steering knob 13 is placed at the end of the path opposite the connection with the path 16. A freely revolving joint 7, e.g., a sphere, which moves freely in a socket is connected to the plunger shaft 4 or between the plunger shaft 4 and the plunger head 3.

6 Claims, 2 Drawing Sheets

SELF-DESTRUCTIVE NON-REUSABLE INJECTION SYRINGE

BACKGROUND OF THE INVENTION

The present invention relates to self-destructive non-reusable injection syringes.

The invention is first and foremost advantageous in connection with non-reusable syringes. Such syringes are used to a large extent by doctors, hospitals, diabetics and others who must have frequent injections. Drug users also compose a large group of users. In connection with the latter group of users, many problems have arisen with the reuse of supposed non-reusable syringes. Diseases which are spread through the transfer of blood, such as hepatitis B and AIDS, recently have become alarmingly widespread because drug users borrow each other's syringes.

Self-destructive injection syringes which have a releasing mechanism which releases after the first use of the syringe are known to exist. The syringes proposed until now have however shown themselves to be too expensive to produce or have been unsafe to use because one has been able to manipulate the syringe in such a manner that the syringe can be used again.

The purpose of the following invention is to produce a non-reusable self-destructive syringe which is inexpensive to produce and which is safe to use; in other words, the syringe is destroyed after the first use, but it can be aired without activating the releasing mechanism.

SUMMARY OF THE INVENTION

The present invention is a self-destructing injection syringe which consists of a cylinder with a needle in one end and a plunger head and plunger shaft, which has a releasing mechanism connected to the plunger head or the plunger shaft. The releasing mechanism releases after the first use of the syringe. The releasing mechanism consists of one part with at least one steering knob which works in coordination with one track or path in another part. This track or path is at an angle to the axis of the syringe and begins at one end of one part. This end of the path is open. The path runs axially to the other end of the part where there is a stopper attached which stops the steering knob from retreating back along the path. There exists also a freely moving joint-link which is connected to the plunger shaft or between the plunger shaft and the plunger head.

A preferred model is one in which the steering knob or knobs are made in one part which is attached to the plunger shaft over the joint link, and the part with the tracks or paths is attached to the piston head.

When an injection is administered with an injection syringe, the syringe must first be filled with the injection fluid by pulling the plunger head up. Next the plunger head is pushed in slightly into the syringe's cylinder with the needle pointing upward until all the air in the syringe is pushed out and the fluid begins to trickle out. The syringe is then put into the skin. Next the syringe must be aspired; i.e., the plunger head is pulled back slightly in order to ensure the correct placement of the needle. If this is an intravenous injection, a little blood will come into the syringe with the pullback of the plunger head. In order to administer this kind of injection with the above-mentioned non-reusable syringe, the preferred model of the invention is characterized by two steering knobs which are situated directly opposite each other at the end of two arms which extend axially from one part of the syringe. A cylindrical body is integrated with the plunger head. An angled path runs toward the plunger head from the part of the cylindrical body which is away from the plunger head. The angled path is attached to another angled path at the end nearest the plunger head and this second path runs in the opposite direction from the first path. The end of the second path which is away from the plunger head is attached to a further angled path which runs parallel to the first angled path. The third angled path is attached to a fourth angled path at the end nearest the plunger head. This fourth path runs parallel to the second path and is open along the cylindrical body's free edge at the end of the path nearest the plunger shaft. The paths are increasing in depth; the first path is not as deep as the second path, the second path is not as deep as the third path, and the third path is not as deep as the fourth path. At each connection of the paths, there is a step down into the next path, which ensures that the steering knob cannot be pulled up a path which has already been travelled.

Further features of the invention are explained in detail in the following text in connection with the drawings which show examples of the above-mentioned injection syringe.

DETAILED DESCRIPTION OF THE DRAWINGS

Figure 1:
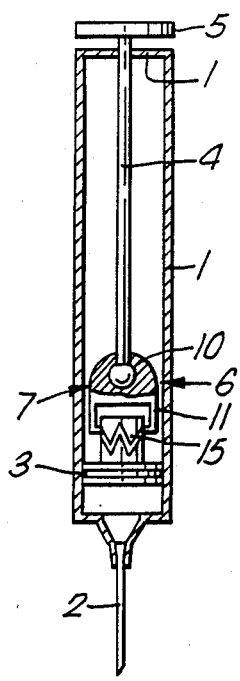
FIG. 1 shows schematically one embodiment of a syringe according to the present invention.

The self-destructive syringe according to the invention consists of cylinder 1 which has one end attached to needle 2. In cylinder 1, the plunger head 3 can be moved along the cylinder with the help of the plunger shaft 4 and the plunger operating knob 5. Plunger shaft 4 is attached to plunger head 3 by a releasing mechanism 6, and the plunger shaft 4 is attached to the releasing mechanism by means of the freely moving joint 7.

Figure 2:
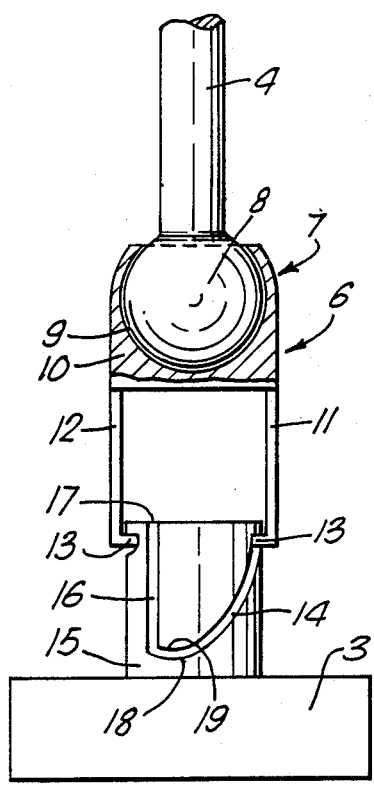
FIG. 2 shows an example of the releasing mechanism and the moving joint-link between the plunger head and the plunger shaft.
Figure 4:
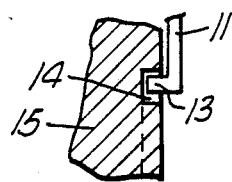
FIG. 4 is a cross-section along line IV—IV in FIG. 3.

As is illustrated in FIG. 2, the freely moving joint 7 consists of sphere 8 which is connected to the lower end of plunger shaft 4. Sphere 8 moves freely in socket 9 which is part of steering knob carrier piece 10. Piece 10 has two projecting arms 11 and 12. At the end of each arm 11 and 12 there are knobs 13 which point radially inward. Each knob 13 runs along path 14 which runs on the outside of cylindrical body 15. Path 14 begins at the free edge of body 15 and runs at an angle toward plunger head 3. At the lower end of body 15, path 14 continues into path 16. Path 16 has an open end 17 at the edge of body 15. An introduction path 16 at the highest edge of body 15 facilitates the introduction of knobs 13 into path 14.

Figure 3:
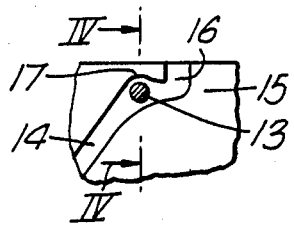
FIG. 3 shows details of the releasing mechanism.

The syringe is assembled in the position which is shown in FIGS. 1 and 2, i.e., with plunger head 3 at the bottom of the syringe and knobs 13 at the top of path 14, so that the knob or knobs 13 lie against the stopped edge 17 at the upper end of path 14 (illustrated in FIG. 3).

The plunger head 3 can thus be pulled up and the injection fluid is pulled into the syringe through the needle which is directed down into the fluid container. Because there is friction between the steering knobs and the path, the syringe can be aired or aspired without the knobs moving along the path. Thereafter, the syringe is put into the tissue and the plunger head is pushed down. The pressure upon the plunger head with the injection of the fluid is so great that the knobs will follow the paths and reach bottom 18 of the path 14. The plunger head 3 now rests at the bottom of the syringe, as is shown in FIGS. 1 and 2, except that the knobs 13 are at the bottom 18 of path 14. If one tries to pull up the plunger head 3 with the help of the plunger shaft 4 and plunger operating knob 5, the knobs 13 which are now located in the position shown by the dotted line will go into path 16 and continue to go out at the open end 17. Because of the freely moving joint 7, the syringe cannot be manipulated in such a way that knobs 13 are directed into path 14 by maneuvering plunger shaft 4. It is further ensured that when plunger shaft 4 is pulled out, knobs 13 will be guided into path 16 because at the lower end of path 14, there is a sloping outwardly guiding edge 19. Edge 19 has its lowest point at the lowest point of path 14. When plunger shaft 4 is pulled out, edge 19 safely ensures that knobs 13 are guided into path 16.

Figure 5:
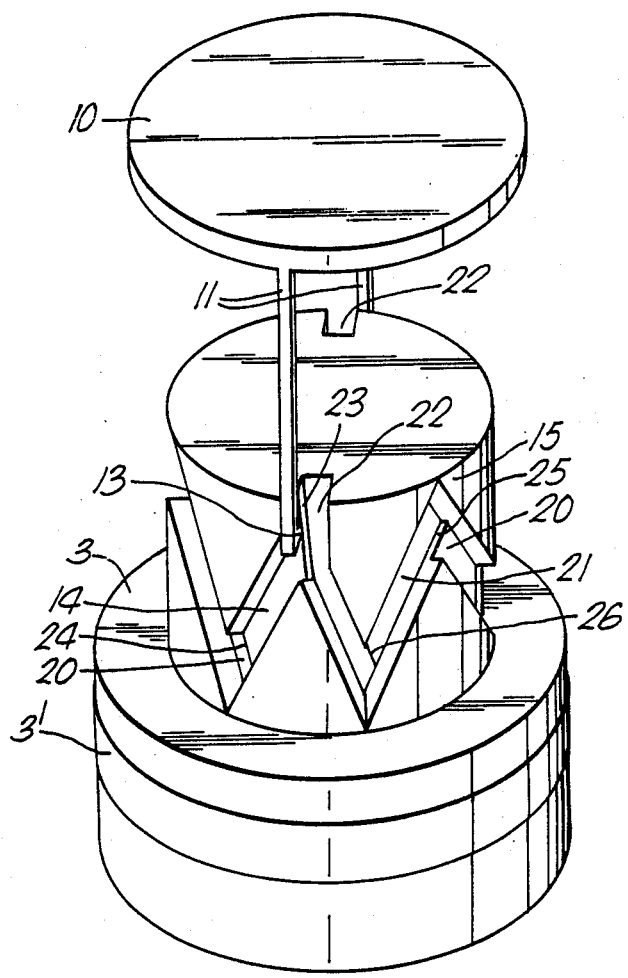
FIG. 5 shows an example which is especially designed for airing and aspiration of the syringe.

FIG. 5 shows the releasing mechanism in a special model where it is possible to air and aspire the syringe without breaking the connection between the plunger head and plunger shaft.

In the same fashion as the previous example, there are two knobs 13 (of which only one is shown) which are attached to the elastic arms 11 which are attached to body 10. These knobs 13 directly face each other.

In the cylindrical body 15, there are two equal paths which are arranged in a zig-zag pattern and which move in correlation with one another. The zig-zag pattern consists of the above-mentioned path 14 which begins at the free edge of body 15 and runs at an angle to plunger head 3. At the end which is nearest to plunger head 3, path 14 is connected to path 20 which runs in an opposite direction to path 14. The end of path 20 which is nearest to the free edge (upper) of body 15 connects to path 21 which runs in the same direction as path 14. The end of path 21 which is nearest to plunger head 3 connects with the fourth path 22 which is open at the free edge of body 15. Path 14 of the second zig-zag pattern connects with path 22 near the free edge of body 15. In the connection between path 14 and path 22, there is a block in the form of a knob or edge 23 at the end of the paths.

When the syringe is assembled, the knobs 13 are directed into the upper end of path 22 so that they axially move over the edge 23 and into path 14. In this position, the plunger head 3 is now in the bottom of the syringe's cylinder 1. The plunger head can be pulled up when the syringe is filled. In order to air the syringe, plunger head 3 is pushed down with the help of plunger operating knob 5. Thereby, the knobs 13 slide first down along each path 14 to the connection point with path 20. Path 14 has decreasing depth from the free edge of body 15 towards the connection point with path 20, such that path 20 has a greater depth than path 14 at the connection between path 14 and path 20. Step 24 is created in this way between path 14 and path 20. In addition, path 20 becomes shallower towards path 21. Path 21 is deeper than path 20 at the connection between path 20 and path 21 such that step 25 is created between path 20 and path 21. In addition, path 21 becomes shallower towards path 22, and step 26 is created in this way between path 21 and path 22. Thus, when the syringe is aired and knobs 13 are guided down each of their paths 14, they will jump down over the edge of the step 24 and down onto path 20. Thereafter, when the plunger shaft is pulled up, knobs 13 follow path 20 and go into path 21 by jumping over the edge of step 25. With the knobs 13 in a connection between path 20 and path 21, the aspiration can be performed, i.e., the plunger head can be pulled back up slightly.

After the aspiration, the injection can be administered by pushing the plunger shaft down. In this way, knobs 13 will follow path 21 and go over edge 26. With the knobs 13 at the connection between path 21 and path 22, the injection can be performed because the knobs 13 lie at the angle between path 21 and path 22 which lies near plunger head 3. The plunger shaft is completely pressed in and the injection is administered. If one tries to refill the syringe by pulling up the plunger shaft, knobs 13 will follow path 22 and will come free from body 15. The connection between plunger shaft 4 and plunger head 3 is thereby broken. A new connection between the plunger shaft 4 and plunger head 3 cannot be made by the manipulation of the syringe because plunger shaft 4 was attached to plunger head 3 by the freely moving joint 7. The plunger shaft 4 with its revolving joint 7, release mechanism 6, and plunger head 3 cannot be pulled out of the syringe without destroying the syringe. This can be done in several ways, for example as is shown in FIG. 2 by the integrated top 1 at the top of the cylinder. In syringes where the plunger shaft 4 has a diameter of the same dimension as the syringe's inner diameter, a top can be made which consists of 2 or more arms which can be inserted into the free space between the arms and the plunger shaft.

The invention is not confined to the above described or to the illustrations shown. For example, the steering knobs may be attached to the plunger head, and the paths can be attached to the plunger shaft. The essence of the invention is the ability to perform a movement in a radial direction through the initial pressure on the plunger shaft, such that the knobs are directed towards the entrance of the axial path which has an open end.

I claim:

1. A self-destructive non-reusable syringe comprising a cylinder with a needle in one end and a plunger head positioned to slide within the cylinder and connected to a plunger shaft by a release mechanism comprising a steering knob carrier rotatably attached to the plunger shaft and having at least one steering knob which runs in a track along the exterior of a protrusion from the plunger head, which track comprises first and second sections, each of which sections is of approximately equal width, the first of which sections runs toward the plunger head along an angle relative to the longitudinal axis of the syringe and the second of which sections runs away from the plunger head substantially along the longitudinal axis of the syringe to an opening, for allowing the plunger head to be drawn from an initial position first away from the needle and then toward the needle and ultimately disengaging the plunger shaft from the plunger head if the plunger shaft is drawn away from the needle for a second time.

2. A syringe according to claim 1 wherein the protrusion from the plunger comprises a cylindrical member coaxial with the longitudinal axis of the syringe, and the track in the protrusion from the plunger head comprises a groove in the side of the protrusion.

3. A syringe according to claim 1 wherein the steering knob engages the track in the protrusion with sufficient friction so that the syringe can be aired and activated without movement of the steering knob along the track.

4. A self-destructive non-reusable syringe comprising:
(a) a cylinder with a needle in one end,
(b) a plunger head positioned to slide within the cylinder toward and away from the needle,
(c) a protrusion attached to the plunger head and having two tracks,
(d) a plunger shaft, and
(e) a release mechanism connecting the shaft to the protrusion, the release mechanism comprising a steering knob carrier rotatably attached to the plunger shaft and having two arms which project toward the plunger from the steering arm carrier and each carry a steering knob attached to the arm end, so that one steering knob is received in each of the tracks,
each of which tracks runs toward and away from the plunger head in a zig-zag path, and each portion of which track is deeper than the preceding portion, so that alternative reciprocation of the steering knob carrier within the cylinder causes each steering knob to travel within its respective track first toward, then away from, then again toward, and finally away from the plunger head and out of the track.

5. A syringe according to claim 4 wherein each steering knob engages its respective track in the protrusion with sufficient friction that the syringe can be aired and activated without movement of the steering knobs along the tracks.

6. A self-destructive non-reusable syringe comprising a cylinder with a needle in one end and a plunger head positioned to slide within the cylinder and connected to a plunger shaft by a release mechanism comprising a steering knob carrier rotatably attached to the plunger shaft and having at least one steering knob which runs in a track in a protrusion from the plunger head, which track comprises first and second sections, the first of which runs toward the plunger head along an angle relative to the longitudinal axis of the syringe and the second section of which is deeper than the first section and runs away from the plunger head substantially along the longitudinal axis of the syringe to an opening, for allowing the plunger head to be drawn from an initial position first away from the needle and then toward the needle and ultimately disengaging the plunger shaft from the plunger head if the plunger shaft is drawn away from the needle for a second time.

* * * * *